US006503535B2

(12) United States Patent
Cappola

(10) Patent No.: US 6,503,535 B2
(45) Date of Patent: *Jan. 7, 2003

(54) METHOD FOR COATING PHARMACEUTICAL DOSAGE FORMS

(75) Inventor: Michael L. Cappola, Wilton, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/754,665

(22) Filed: Jan. 4, 2001

(65) Prior Publication Data

US 2001/0012519 A1 Aug. 9, 2001

Related U.S. Application Data

(62) Division of application No. 09/494,099, filed on Jan. 28, 2000, now Pat. No. 6,254,888.

(51) Int. Cl.⁷ .............................. A61K 9/28; A61K 9/30; A61K 9/36; B01J 13/00
(52) U.S. Cl. ...................... 424/474; 424/475; 424/479; 424/480; 427/2.14
(58) Field of Search .................. 424/451, 458, 424/459, 460, 461, 464, 467, 474, 475, 479, 480; 427/2.14

(56) References Cited

U.S. PATENT DOCUMENTS

| | | | | |
|---|---|---|---|---|
| 3,655,852 A | * | 4/1972 | Koff et al. | 264/115 |
| 3,835,221 A | * | 9/1974 | Fulberth et al. | 424/20 |
| 4,255,438 A | * | 3/1981 | Kane et al. | 424/273 |
| 5,389,380 A | | 2/1995 | Noda et al. | |
| 5,464,833 A | | 11/1995 | Nakai et al. | |
| 5,645,858 A | | 7/1997 | Kotwal et al. | |
| 5,897,910 A | | 4/1999 | Rosenberg et al. | |

FOREIGN PATENT DOCUMENTS

| | | | |
|---|---|---|---|
| EP | 0 023 327 A | | 2/1981 |
| EP | 0023327 | * | 4/1981 |
| EP | 0 439 315 A1 | | 7/1991 |
| EP | 0 508 653 A1 | | 10/1992 |
| EP | 0 659 432 A1 | | 6/1995 |
| EP | 0659432 A1 | * | 6/1995 |
| FR | 2 363 325 A | | 3/1978 |
| GB | 2195248 | * | 4/1988 |
| GB | 2 195 248 A | | 4/1988 |
| WO | 93/00073 | * | 1/1993 |
| WO | WO93 00073 A | | 1/1993 |
| WO | WO00 57838 A | | 10/2000 |
| WO | 00/57838 | * | 10/2000 |

OTHER PUBLICATIONS

Riverside Webster's II, New College Dictionary, 1995, p. 683.*

* cited by examiner

Primary Examiner—Thurman K. Page
Assistant Examiner—S. Tran
(74) Attorney, Agent, or Firm—Robert P. Raymond; Philip I. Datlow; Alan R. Stempel

(57) ABSTRACT

The invention provides a process for coating a branded pharmaceutical dosage form for the purpose of covering any embossed or printed matter or any colored coating by the application of an amount of a sugar based coating which is sufficient to obscure any identifying indicia without compromising the stability or releasability of the drug that is contained in the dosage form.

18 Claims, No Drawings

METHOD FOR COATING PHARMACEUTICAL DOSAGE FORMS

This application is a divisional of U.S. application Ser. No. 09/494,099, filed Jan. 28, 2000 now Pat. No. 6,254,888, herein incorporated by reference in its entirety.

BACKGROUND OF THE INVENTION

The present invention relates to a method for manufacturing placebo tablets or positive control tablets that are identical to tablets that contain active drugs. Clinical studies to determine the effectiveness of new drugs requires that identical tablets be prepared which contain an active drug, no drug (placebo) and/or a control drug. This is done in order to prevent the patients and investigators from knowing who is receiving the drug that is being tested and for this reason the clinical studies are usually referred to as being "double blind". This is because neither the investigator nor the patient can tell from the packaging which dosage form is the new drug.

In the prior art when a drug manufacturer carried out a test of a product against a competitor's patented product, it was not unusual to request that the competitor prepare a blinded supply of the product. This would usually be done if the study protocol and results were shared with the competitor.

In the prior art, blinded samples have been prepared by over encapsulation, coating or debranding. Over encapsulation is a process whereby a dosage form, which is usually a tablet, is placed in a capsule. This procedure requires in some cases the use of an oversize capsule which may be difficult to swallow. This process is time consuming and strict quality controls are required to assure that the capsule and tablet are bioequivalent and are manufactured properly. The gelatin and moisture in the capsules may introduce stability problems. Overcoating of tablets has not been successful for embossed tablets because of the formation of ghost images in the areas where the tablets are embossed. The debranding of printed tablets and capsules is a labor intensive process that may raise the question of stability due to the use of solvents for manually deinking the printed matter on the dosage form.

When compendium products are involved, a generic formulation may have to be prepared which requires a development project where stability and bioequivalence have to be demonstrated.

A further alternative is a mill and fill process where tablets are milled and filled into capsules. This procedure maximally disturbs the original dosage form and questions relative to equivalence uniformity, stability and bioavailability must be resolved.

The applicant has devised a process of coating branded dosage forms which does not compromise the integrity of the branded pharmaceutical dosage form but provides an overcoat that is sufficient to cover all product indicia without interfering with the stability or the releasability of the drug.

The invention also provides a method for coating micro tablets for the purpose of "rounding" the micro tablets to facilitate the mechanical filling of the micro tablets into capsules; a method of isolating incompatible ingredients in micro tablets and a method of incorporating an additional active ingredient into the micro tablet. As used herein a micro tablet is a tablet which is generally considered to be less than 4 mm in diameter (if round) or less than 4 mm in longest dimension. They are prepared with the same ingredients as traditional tablets and capsules which include lactose, starch, microcrystalline cellulose, disintegrants, flow agents and lubricants.

SUMMARY OF THE INVENTION

The invention provides a process for coating a branded pharmaceutical dosage form for the purpose of covering any embossed or printed matter or any colored coating by the application of an amount of coating which is sufficient to obscure any identifying indicia without compromising the stability or releasability of the drug that is contained in the dosage form.

The invention also provides a method of coating a micro tablet to form a rounded tablet which may comprise any or all of the following:
 (a) sealing said micro tablet by applying a seal coat to form a sealed micro tablet;
 (b) applying to said micro tablet an effective amount of a coating which provides a smooth coating over said micro tablet to provide a smoothly coated micro tablet; and
 (c) polishing the tablet to form a polished and moisture resistant pharmaceutical dosage form.

A method of separating incompatible micro tablets is disclosed which may comprise any or all of the following:
 (a) sealing the incompatible micro tablet by applying a seal coat to form sealed incompatible micro tablet;
 (b) applying to said micro tablet an effective amount of coating which provides a smooth coating over micro tablet to provide a smoothly coated micro tablet; and
 (c) polishing the coated micro tablet to form a polished and moisture resistant pharmaceutical dosage form.

In addition, there is disclosed a method of incorporating additional active ingredients into a micro tablet, said method may comprise any or all of the following:
 (a) coating an active ingredient onto a micro tablet using a solution or suspension of said active ingredient to form a coated micro tablet;
 (b) sealing said micro tablet by applying a seal coat to form a sealed micro tablet;
 (c) applying to said sealed micro tablet an effective amount of a coating which provides a smooth coating over said micro tablet to provide a smoothly coated micro tablet; and
 (d) polishing the smoothly coated micro tablet of step (c) to form a polished and moisture resistant pharmaceutical dosage form.

Accordingly, it is a primary object of the invention to provide a novel method of obscuring the identifying indicia on a pharmaceutical dosage form.

It is also an object of the invention to provide a method of obscuring the printed matter or indicia on a pharmaceutical dosage form without compromising the stability or bioavailability of the pharmaceutical dosage form.

It is also an object of the invention to provide a cost efficient process for obscuring the embossed or printed matter on a pharmaceutical dosage form.

These and other objects of the invention will become apparent from the present specification.

DETAILED DESCRIPTION OF THE INVENTION

The invention is primarily intended to be applicable to embossed tablets but may be used for coated/printed tablets or capsules or micro tablets.

The first step in the process of the invention is a sealing step that may be carried in a traditional coating pan or in another coating apparatus that is used in the pharmaceutical arts. A high molecular weight polyethylene glycol (e.g. polyethylene glycol 8000 or similar type material) is melted onto the core tablets in such a manner and amount to provide a seal coat around the tablet and to partially or fully cover and/or fill any depressions or elevations of the indicia. Even though the polymer is water soluble, due to its high molecular weight its rate of solution is slow enough to afford the core tablets moisture protection during the process. The polyethylene glycol may be substituted with any polyethylene glycol which is solid at room temperature (25° C.). Other polymers, which offer similar water solubility and a similar degree of moisture protection from the latter coating solutions, may be used. An example of this would be substituted polaxamers that are solid at room temperature. Additionally, agents such as beeswax, shellac, cellulose acetate phthalate, polyvinyl acetate phthalate, zein, film forming polymers such as hydroxypropyl cellulose, ethylcellulose and polymeric methacrylates can be dissolved in a suitable solvent and applied to the embossed or printed tablets, and may be used, provided that the coating has no substantial effect on the disintegration/dissolution of the dosage form and that the coated dosage form is physiochemically stable.

Solid polyethylene glycol is preferably applied to the core tablet using a 100% solids concentration and a temperature sufficient to melt the polymer and cause it to spread. A melt application process is preferred because this prevents any solvent or water from attacking the pharmaceutical dosage form during or after the initial sealing process. Generally from 1 to 10% by weight, based on the total weight of the tablets, of the dry polymer is applied to seal the tablets. Higher or lower amounts may also be employed. Since the coating efficiency is about 50%, when 10% of a sealing polymer is applied, the weight gain on the tablet will be approximately 5% based on the total weight of the tablets and the dried coating.

After the dosage form is sealed, a sugar coating may be applied onto the sealed pharmaceutical dosage form by the application of a plurality of coats of a low solids (or the like), sugar coating solution (or the like). The low solids sugar solution (or the like) is preferred to ensure that the coating of any embossed or printed surfaces will result in a smooth coating and may comprise sucrose, lactose, dextrose, sorbitol and the like or mixtures thereof. If desired, colorants or opacifiers may be added to the sugar solution. The low solids solutions may comprise from about 30 to 50% by weight of water.

The dusting powder may comprise an antisticking agent such as talc, starch, kaolin, etc. in combination with a sugar such as lactose or dextrose or the like to be used during the sugar coating process to control sticking and to assist in the formation of a rounded smooth surface on the pharmaceutical dosage form.

A 1:1 mixture of lactose:talc (soluble:insoluble ratio of ingredients) is used to minimize negative dissolution effects that may occur if higher amounts of insoluble agents are used. However, different ratios of soluble and insoluble agents may be used if this is not problematic. The final coats may be applied without the aid of any antisticking agent to provide a final smooth effect on the pharmaceutical dosage form prior to the final application of a polishing solution which may comprise a solution of a polymer such as polyethylene glycol 8000 in water and ethanol to provide a non-sticky, aesthetically pleasing surface on the finished product. Other solids which may be used in the polishing solution include waxes, polaxamers, hydroxypropylcellulose, hydroxycellulose, ethylcellulose or the polymeric methacrylates.

The following description of a preferred method for practicing the invention is set forth to illustrate the invention and not as a limiting description as to how the invention may be practiced.

A charge of core tablets, marked with a printed-indicia, which are sufficient to fill the lower volume of a coating pan, without falling out during rotation are placed into the pan (1.3 kg. of tablets in a pan having an 8" front opening diameter). The pan is rotated and heat from a hot air gun and a infrared light is applied to raise the temperature to about 65–70° C.

Powdered polyethylene glycol (PEG) 8000 at an amount calculated to provide a total weight gain of 2.5% is added to the coating pan and heat is applied to the rotating pan until the powdered PEG is melted. Cooling air may be used if the tablets start to slide rather than tumble as the pan is rotated. A rotation speed of 4–12 rpm may be used initially for heating and the rotation set at about 32 rpm during the application of the PEG powder. Subsequently, the rotation speed is lowered to 22 and then to 14 rpm after the PEG is melted. When the seal coat is dry to the touch, the sealed tablets are removed from the coating pan and the pan is washed to remove the residue of PEG from the pan to prevent any PEG from being present in the next coating layer.

The tablets are placed in the cleaned pan and alternate applications of the coating syrup and the dusting powder are applied.

The coating syrup and the dusting powder are as follows:

| Coating Syrup % w/w | Dusting Powder % w/w |
| --- | --- |
| 50 sucrose | 50 lactose |
| 15 lactose | 50 talc |
| 35 water | |

The first 5 to 10 applications (rounding stage) of the syrup/dusting powder coatings are critical to prepare the tablets for the subsequent steps in the process. The syrup volumes are relatively large and for example a 1.3 kg batch of tablets would required 10–30 ml of syrup followed by 5–30 g of dusting powder. The coating application (syrup/dusting powder) is carried out at room temperature with the optional use of forced air into the coating pan to aid in drying the tablets. Rotational speed is adjusted to avoid sticking and to optimize the smoothness of the tablets. At the completion of the "rounding" (coating process) the tablets should easily tumble in the coating pan and any embossing or printed matter should be significantly obscured. Typically 5–10 applications of the syrup/dusting powder coating materials will be sufficient but the nature of the embossing may require further coating of the tablets. The later applications of syrup alone during the smoothing step would require about 5–30 ml of syrup for each application of the coating syrup.

At the end of the rounding stage, the dried tablets are removed from the pan and the pan is washed for the next stage which is smoothing. During smoothing the tablets slowly fill in the remaining embossing and scores (if necessary) and a smooth overall appearance is attained.

Numerous coats of the syrup solution are applied and the rotational speed of the pan is adjusted to permit the tablets to tumble without dusting. Forced room temperature air may be used in the final stage of drying. An example of this would be the application of 5 ml of syrup solution at a pan rotation of 32 rpm. When the tablets tumble freely, the pan rotation is reduced to 22 rpm and then to 14 rpm. Forced air may then be applied until the tablets are dry and the forced air is removed prior to tablet polishing. Subsequent coats are applied until there is no remaining indicia of the original tablet indicia. This usually requires about 20 to 30 coats. The average tablet weight increases after rounding and smoothing by about 25% to 125% based on the combined weight of the original tablet and the dried coating.

When the smoothing stage is completed, the tablets are removed for drying in trays or under ambient conditions. The pan is washed in preparation for the final polishing stage. Polishing is necessary to provide some protection for the sugar layers during handling so the tablets do not feel sticky to the touch. The tablets are placed in the cleaned pan and a solution of 45% w/w of PEG 8000; 33% w/w of ethanol and 22% w/w of water are added in 5–10 ml increments while the pan is rotated at 32 rpm with additional hand stirring with a spatula. Forced air is applied if the tablets begin to slide rather than tumble in the pan. The speed of the pan is adjusted as the tablets begin to tumble in order to cause the surface of the tablets to become smoother. Gradual reduction of the pan speed to 22, 14, 12, 8, 4 rpm is used to increase the smoothness. Usually a total of 8–10 applications of the polishing solution will provide a satisfactory finish. The final polishing step may be carried out in a conventional cloth lined pan or manually polished. The average weight increase due to polishing is from 0.5 to 5% by weight based on the combined weight of the tablets and the dried polishing agents.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A method of coating a micro tablet to form a rounded tablet which comprises:
   (a) melting a 100% solids pharmaceutically acceptable polymer by heating the polymer to a temperature sufficient to melt the polymer;
   (b) sealing a micro tablet by applying a seal coat of the melted 100% solids pharmaceutically acceptable polymer produced in step (a) on the micro tablet to form a sealed micro tablet;
   (c) applying to said sealed micro tablet an effective amount of a coating which provides a smooth coating over said micro tablet to provide a smoothly coated micro tablet; and
   (d) polishing the smoothly coated micro tablet of step (c) to form a polished and moisture resistant microtablet.

2. A method of separating incompatible micro tablets which comprises:
   (a) melting a 100% solids pharmaceutically acceptable polymer by heating the polymer to a temperature sufficient to melt the polymer;
   (b) sealing each of the incompatible micro tablets by applying a seal coat of the of the melted 100% solids pharmaceutically acceptable polymer produced in step (a) on the micro tablet to form a sealed incompatible micro tablet;
   (c) applying to said sealed micro tablet an effective amount of a coating which provides a smooth coating over said micro tablet to provide a smoothly coated micro tablet; and
   (d) polishing the smoothly coated micro tablet of step (c) to form a polished and moisture resistant microtablet.

3. A method of coating micro tablets to form rounded micro tablets as set forth in claim 1, further comprising the step of filling the rounded micro tablets into capsules.

4. A method as defined in claim 1, wherein the pharmaceutically acceptable polymer in step (a) is water-soluble.

5. A method as defined in claim 1, wherein the coating of step (c) is applied using a low solids sugar solution comprising about 30 to 50% by weight of water.

6. A method as defined in claim 2, wherein the pharmaceutically acceptable polymer in step (a) is water-soluble.

7. A method as defined in claim 2, wherein the coating of step (c) is applied using a low solid sugar solution comprising about 30 to 50% by weight of water.

8. A method as defined in claim 1, wherein the pharmaceutically acceptable polymer in step (a) is a polyethylene glycol or substituted poloxamer.

9. A method as defined in claim 2, wherein the pharmaceutically acceptable polymer in step (a) is a polyethylene glycol or substituted poloxamer.

10. A method of coating and blinding a branded micro tablet to form a rounded micro tablet which comprises:
    (a) sealing a branded micro tablet having thereon embossed, printed or colored indicia by applying a seal coat of a melted 100% solids pharmaceutically acceptable polyer on the branded micro tablet to form a sealed micro tablet;
    (b) applying to said sealed micro tablet an effective amount of a coating which provides a smooth coating over said micro tablet to provide a smoothly coated micro tablet; and
    (c) polishing the smoothly coated micro tablet of step (b) to form a polished a moisture resistant microtablet.

11. A method of blinding and separating branded incompatible micro tablets which comprises:
    (a) sealing each of the branded incompatible microtablets having thereon embossed, printed or colored indicia by applying a seal coat of a melted 100% solids pharmaceutically acceptable polymer on the branded micro tablet to form a sealed incompatible micro tablet;
    (b) applying to said sealed micro tablet an effective amount of a coating which provides a smooth coating over said micro tablet to provide a smoothly coated micro tablet; and
    (c) polishing the smoothly coated tablet of step (b) to form a polished and moisture resistant microtablet.

12. A method of coating micro tablets to form rounded micro tablets as set forth in claim 10, further comprising the step of filling the rounded micro tablets into capsules.

13. A method as defined in claim 10, wherein the pharmaceutically acceptable polymer in step (a) is water-soluble.

14. A method as defined in claim 11, wherein the pharmaceutically acceptable polymer in step (a) is a polyethylene glycol or substituted poloxamer.

15. A method as defined in claim 10, wherein the coating of step (b) is applied using a low solids sugar solution comprising about 30 to 50% by weight of water.

16. A method as defined in claim 11, wherein the pharmaceutically acceptable polymer in step (a) is water-soluble.

17. A method as defined in claim 11, wherein the pharmaceutically acceptable polymer in step (a) is a polyethylene glycol or substituted poloxamer.

18. A method as defined in claim 11, wherein the coating of step (b) is applied using a low solids sugar solution comprising about 30 to 50% by weight of water.

* * * * *